United States Patent
Bond et al.

(10) Patent No.: US 12,140,539 B2
(45) Date of Patent: Nov. 12, 2024

(54) METHOD FOR DETERMINING RINSE PROPERTIES

(71) Applicant: Conopco, Inc., Englewood Cliffs, NJ (US)

(72) Inventors: Sinead Elizabeth Bond, Liverpool (GB); Lynsey Joanne Coan, Wirral (GB); Raquel Gutierrez-Abad, Manchester (GB); Jun On Jamie Yip, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 278 days.

(21) Appl. No.: 17/769,854

(22) PCT Filed: Nov. 4, 2020

(86) PCT No.: PCT/EP2020/080896
§ 371 (c)(1),
(2) Date: Apr. 18, 2022

(87) PCT Pub. No.: WO2021/104811
PCT Pub. Date: Jun. 3, 2021

(65) Prior Publication Data
US 2022/0381688 A1  Dec. 1, 2022

(30) Foreign Application Priority Data
Nov. 29, 2019  (EP) .................... 19212673

(51) Int. Cl.
*G01N 21/51* (2006.01)
*G01N 21/47* (2006.01)
*G01N 21/49* (2006.01)

(52) U.S. Cl.
CPC ............ *G01N 21/51* (2013.01); *G01N 21/49* (2013.01); *G01N 21/47* (2013.01)

(58) Field of Classification Search
CPC .... G01N 21/49; G01N 21/47; G01N 21/4737; G01N 21/51
See application file for complete search history.

(56) References Cited

U.S. PATENT DOCUMENTS

| | | | |
|---|---|---|---|
| 5,928,657 A | 7/1999 | Simon | |
| 2002/0037267 A1 | 3/2002 | Guillou et al. | |
| 2015/0276594 A1 * | 10/2015 | Johnson | G01N 21/51 356/338 |
| 2017/0145669 A1 | 5/2017 | Klicpera et al. | |

FOREIGN PATENT DOCUMENTS

| | | | |
|---|---|---|---|
| CN | 102090852 | 6/2011 | |
| CN | 106821257 | 2/2019 | |
| DE | 10156924 A1 * | 6/2003 | ......... A47L 15/4297 |
| DE | 112015006237 | 11/2017 | |
| EP | 2471988 | 7/2012 | |
| EP | 3034676 | 6/2016 | |
| GB | 2208297 | 3/1989 | |
| IN | 01452KO2013 | 12/2013 | |
| JP | 2011200522 | 10/2011 | |
| WO | WO-0008465 A2 * | 2/2000 | ............ G01N 21/82 |
| WO | WO2005107699 | 11/2005 | |
| WO | WO-2012010745 A1 * | 1/2012 | ............ B01D 21/01 |
| WO | WO2013092708 | 6/2013 | |
| WO | WO2014016351 | 1/2014 | |
| WO | WO-2014016352 A2 * | 1/2014 | ............... A61K 8/04 |
| WO | WO2014016353 | 1/2014 | |
| WO | WO2014016354 | 1/2014 | |
| WO | WO2015018853 | 2/2015 | |
| WO | WO2015109910 | 7/2015 | |
| WO | WO-2021055309 A1 * | 3/2021 | ............... B05B 1/08 |

OTHER PUBLICATIONS

Extended European Search Report and Written Opinion on EP19212673 dated May 13, 2020.
International Search Report and Written Opinion on PCT/EP2020/080896 dated Jan. 25, 2021.
International Preliminary Report on Patentablity on PCT/EP2020/080896 dated Oct. 27, 2021.

* cited by examiner

*Primary Examiner* — Jonathan M Dunlap
(74) *Attorney, Agent, or Firm* — Byrne Poh LLP; Nina R. Horan

(57) ABSTRACT

A method of measuring rinse properties of a composition from a surface, the method includes providing a cosmetic treatment composition. The method also includes applying the cosmetic treatment composition to a surface. The method also includes rinsing the surface with a first amount of water after applying the cosmetic treatment composition to the surface. The method also includes collecting a portion of the first amount of water after rinsing the surface with the first amount of water. The method also includes measuring a first turbidity of the portion of the first amount of water after collecting the portion of the first amount of water.

19 Claims, No Drawings

METHOD FOR DETERMINING RINSE PROPERTIES

CROSS-REFERENCE TO RELATED APPLICATIONS

This application claims priority to International Patent Application No. PCT/EP2020/080896, filed on Nov. 4, 2020, and European Patent Application No. 19212673.8, filed on Nov. 29, 2019, both of which are incorporated herein by reference in their entireties.

FIELD OF INVENTION

The present invention relates to method for determining rinse properties of compositions, having particular application in the field of hair care.

BACKGROUND AND PRIOR ART

Many products, formulated for use on surfaces, are designed to be rinsed off during use. Such products include shampoos and conditioning compositions for use on hair. These may be used as part of a hair care regime such as a daily wash and care process. These products often deposit benefit agents, for example silicones, onto the hair surface. Other, leave on, compositions deposit benefit agents onto hair that remain on the hair until the hair is next washed.

The rinsing of a composition from a surface is an important phenomenon. It can affect the way a consumer perceives product performance or makes the decision about whether to stop or continue rinsing. Rinsing properties of hair treatment compositions affect the length of time that a consumer rinses his/her hair and so directly influence, ipso facto, the amount of water that a consumer uses when using a rinse-off product.

It is known to measure the amount of foam and correlate to rinsing properties.

WO 15/018853 discloses cosmetic compositions containing silicones to facilitate rinsing. Methods to measure the impact on the rinsing stage include the measurement of time needed to remove the lather, or the count of buckets or amounts of water needed.

WO 05/107699 discloses foam cleansers with suspended particles. A test to determine the ability to rinse foam from hands until the foam has disappeared is described.

GB 2 208 297 discloses liquid detergent compositions for laundry, household cleaning, hair and body. A rinsability test that uses measured quantities of water until no surfactant foam is seen is used.

We have, however, found that foam tracking methods have several disadvantages. Foam is sensitive to factors such as water temperature, flow rate and time. For example, foam volume can change with these variables, making such methods less accurate and difficult to reproduce. Different operators may visually assess the amount of foam differently.

IN 01452KO2013 discloses a quantitative method to measure the rinsability of cleansing formulations by measuring the conductivity of the post wash water. A formulation is applied to skin in-vivo and wash water is applied in repeated aliquots. A standard conductivity score card is then used to obtain a rinsability rating for the formulation.

US 2002/037267 discloses a foaming cleansing composition, which is a transparent gel. Turbidity is used to measure the transparency of the composition itself. Foam quality upon rinsing is investigated as ease of removal of a slippery film from the hands.

U.S. Pat. No. 5,928,657 discloses cosmetic compositions for cleaning the skin and improving the rinsability of the oily gel compositions. Turbidity is used to characterise the behaviour of the gel composition itself after dispersing the gel in water in a flask.

Despite the prior art there remains a need for a method for determining rinse properties of compositions that is accurate, reliable and accessible and that can be quickly and easily carried out.

We have found that by measuring the turbidity of water used to rinse a composition off a hair surface during or after rinsing, we can provide a reliable and accessible way of predicting rinse properties of compositions, with superior accuracy. It is possible, using this method, to determine when no further composition is coming off the hair and thus to determine the end point of the rinse.

STATEMENT OF INVENTION

In a first aspect, the invention provides a method of measuring rinse properties of a composition from a human surface, comprising the steps of:
  i) providing a cosmetic treatment composition;
  ii) applying the composition of (i) to the surface;
  iii) rinsing the surface with water;
  iv) collecting the rinse water;
  v) optionally repeating steps iii)-iv); and
  vi) measuring the turbidity of the collected rinse water, until constant turbidity is reached.

A preferred method includes a step of correlating the turbidity of the collected rinse water to the amount of water used to rinse the surface. Preferably, the turbidity of the rinse water is compared with that of pure water.

Preferably, the method includes the step of repeating steps iii)-vi), preferably at a set time interval. Preferably, the time interval is from 4 to 120 seconds, more preferably from 5 to 60 seconds, most preferably from 5 to 20 seconds. Preferably, steps iii)-iv) are repeated until turbidity reaches zero.

The surface is rinsed with water. The water may be applied as a flow or as discrete quantities such as aliquots. Preferably a flow of water is used, preferably having a constant flow rate. The temperature of the water may also influence the rate of rinsing and is preferably kept constant throughout the method.

Constant turbidity is when turbidity remains approximately constant. This is shown by the formation of a plateau in the changes to the turbidity in sequential measurements. There may still be some changes but these are small enough to indicate that only a very little amount of composition is being removed.

Constant turbidity may be determined by noting when sequential turbidity measurements are not significantly different from each other.

Constant turbidity indicates the end point of the rinsing of the composition from the human surface.

GENERAL DESCRIPTION OF THE INVENTION

The Method

The method of the invention measures the rinse properties of a composition. The rinse properties are related to the quantity of water required to rinse the composition from a surface.

The composition is a cosmetic composition. A cosmetic composition, for example, a personal care composition, is intended for application to the human body, particularly the skin or hair. Preferably the composition is selected from a hair composition (for example a hair cleansing composition, a hair conditioning composition or a hair styling composition) and a skin composition (for example, a skin cleansing composition or a skin conditioning composition).

Advantageously, the method of the invention may be used to compare rinse properties of different compositions, for example a composition before and after a modification to the composition has been carried out. This is accomplished by carrying out the method using a first treatment composition and then carrying out the method using a second treatment composition.

Preferably, the method includes repeating steps (i) to (vi) for a second treatment composition and comparing the rinse properties of the first and second treatment compositions to determine the relative rate of rinsing of the first and second treatment compositions. The composition having the greater reduction in turbidity after rinsing, is rinsed faster from the surface and requires less water to be rinsed from the surface.

Turbidity may be measured using any suitable technique. A preferred method involves using a turbidimeter, for example a Turbiscan TLab Expert. The turbidity is suitably measured relative to clear water.

The Treatment Composition

The composition is preferably formulated as a rinse off composition.

Preferably, the composition is structured. By structured is meant it comprises a molecular orientation that forms a gel phase or a lamellar phase.

The composition is preferably a hair treatment composition.

Rinse off hair treatment compositions for use in the present invention are preferably selected from a shampoo and a conditioner, most preferably a conditioner.

Compositions for use in the method of the invention are preferably formulated as conditioners for the treatment of hair (typically after shampooing) and subsequent rinsing.

Preferred conditioners comprise a conditioning base. The conditioning base preferably forms a gel phase.

Treatments compositions for use in the method of the current invention preferably comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula

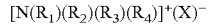

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the alkyl chain lengthy is $C_8$ to $C_{14}$.

Suitable examples of such materials correspond to the formula

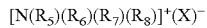

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quaternary ammonium compounds of the above general formula for use in compositions for use in the method of the invention include:

(i) Lauryl trimethylammonium chloride (available commercially as Arquad C35 ex Akzo); cocodimethyl benzyl ammonium chloride (available commercially as Arquad DMCB-80 ex-Akzo)

(ii) Compounds of the formula:

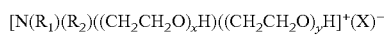

wherein:
x+y is an integer from 2 to 20;
$R_1$ is a hydrocarbyl chain having 8 to 14, preferably 12 to 14, most preferably 12 carbon atoms and containing ether, ester, amido or amino moieties present as substituent's or as linkages in the radical chain;
$R_2$ is a $C_1$-$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the formula:

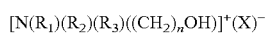

wherein:
n is an integer from 1 to 4, preferably 2;
$R_1$ is a hydrocarbyl chain having 8 to 14, preferably 12 to 14, most preferably 12 carbon atoms;

R₂ and R₃ are independently selected from $C_1$-$C_3$ alkyl groups, and are preferably methyl, and X— is a salt-forming anion such as those selected from halogen, (e.g. chloride, bromide), acetate, citrate, lactate, glycolate, phosphate nitrate, sulphate, alkylsulphate radicals. Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2014/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

A Viscosity Reduction Agent

Preferably, the method of the invention includes a step of adding a viscosity reduction agent to the neat treatment composition to reduce the viscosity.

A preferred viscosity reduction agent is a hydrophobically modified anionic polymer Preferably, the hydrophobically modified anionic polymer is an acrylate or methacrylate polymer.

Preferably, the hydrophobic modification comprises alkylation. Preferably, the alkyl group comprises from 6 to 30 carbons, more preferably from C12 to C30, even more preferably from 16 to 28 and most preferably from 18 to 24 carbons.

A preferred polymer is sold by Rohm & Haas under the tradename Aculyn, the most preferred of which is Aculyn 28™.

The polymer is preferably added at a level of from 0.01 to 5 wt %, more preferably from 0.02 to 0 5 wt %, even more preferably from 0.03 to 4 wt % and most preferably from 0.05 to 4 wt %, by total weight of the hair treatment composition.

Preferably, the surface is a hair surface.

EXAMPLES

Embodiments of the invention will now be illustrated in the following examples, in which amounts are given by weight of the total composition, unless otherwise stated.

Example 1: Compositions A, B, C and D, for Use in the Method of the Invention

The following hair conditioner compositions were prepared:—

Compositions A-D were hair conditioners. A and C comprise as Acrylates/Beheneth-25 Methacrylate Copolymer, which increases the rate of rinse from the surface of the hair.

TABLE 1

Compositions of conditioners A and B for use in the method of the invention

| Ingredient | A Quantity [wt %] | B Quantity [wt %] |
|---|---|---|
| Cetearyl Alcohol | 3.2 | 3.2 |
| Behenyltrimonium Chloride | 2.3 | 2.3 |
| Conditioning silicone | 1.4 | 1.4 |
| Fragrance | 0.6 | 0.6 |
| Acrylates/Beheneth-25 Methacrylate Copolymer | 0.25 | — |
| UV Fluorescer (Tinopal CBS-X ex BASF) | 0.1 | 0.1 |
| Preservative | 0.1 | 0.1 |
| water | To 100 | To 100 |

TABLE 2

Compositions of conditioners C and D for use in the method of the invention

| Ingredient | C Quantity [wt %] | D Quantity [wt %] |
|---|---|---|
| Behentrimonium Chloride | 1.4 | 1.4 |
| Cetearyl Alcohol | 3.1 | 3.1 |
| Conditioning silicone | 1.4 | 1.4 |
| Stearamidopropyl Dimethylamine | 0.3 | 0.3 |
| Fragrance | 0.6 | 0.6 |
| Acrylates/Beheneth-25 Methacrylate Copolymer | 0.500 | — |
| Lactic Acid 88% | 0.1 | 0.1 |
| Sodium Chloride | 0.1 | 0.1 |
| Preservative | 0.1 | 0.1 |
| UV Fluorescer (Tinopal CBS-X ex BASF) | 0.1 | 0.1 |
| Water | To 100 | To 100 |

The conditioners A-D were prepared using the following methods:
1. Water was added to a suitable vessel, lactic acid (if present) and copolymer (if present) were added, and the vessel heated to 80° C. The UV fluorescer was added.
2. Cetearyl alcohol was then added to the formulation along with tertiary amine salt (if present)
3. At 80° C. the Behenyltrimmonium Chloride was added (if present) and the resultant mixture mixed.
4. The heat was then turned off and quench water added.
5. The mixture was then cooled to below 40° C. and the rest of the materials were added.
6. Finally, the formulation was mixed at high shear on a Silverson mixer at 5000 rpm for 5 minutes.

Example 2: Measurement of Turbidity of the Rinse Water from Hair Following Treatment with Compositions A-D The hair used in the following examples was dark brown European hair in 5 g 10" switches.
1. Hair switches were pre-washed with 14% SLES-1EO solution to remove any surface contamination before starting any treatment. Each switch was treated with 0.1 mL solution per g of hair and lathered for 30 s before being rinsed in warm water (35° C.-40° C., flow-rate 4 L min−1) for 30 s. Excess water was removed by running the switch between finger and thumb under light pressure
2. 2.5 g of conditioner A, B, C or D was applied onto the switch and spread evenly across the surface of the switch.
3. The switch was fastened onto a clamp by metal clip and a container positioned below the switch.
4. Water was applied to the switch (at a flow rate of approx. 1 L/min) and collected in the container. Water was applied to the switch for the following timepoints (10/20/25/30/35 and 40 seconds), with the water running off the switch during each timepoint being collected in a separate glass jar. Stopwatch and water flow were stopped at each timepoint to allow collection of water and placement of new container beneath the switch.

Three replicates were carried out for each formulation (using a new hair switch for each replicate).

The turbidity of the collected rinse water samples was measured using a Turbiscan TLab Expert, at 25° C. The values from the Turbiscan were captured as $\Delta T$, relative to clear water.

The results are given in Table 3 below.

TABLE 3

Turbidity /$\Delta T$ (mean of 3 replicates) of rinse water from hair treated with compositions A-D

| Rinse time (s) | A Mean | A SD | C Mean | C SD | D Mean | D SD | B Mean | B SD |
|---|---|---|---|---|---|---|---|---|
| 5 | 79.67 | 4.51 | 79.00 | 3.61 | 39.67 | 30.66 | 39.67 | 20.11 |
| 10 | 64.67 | 15.01 | 41.33 | 10.07 | 30.67 | 19.14 | 32.00 | 13.08 |
| 15 | 43.00 | 9.85 | 17.67 | 15.04 | 48.00 | 12.12 | 37.67 | 21.08 |
| 20 | 28.33 | 16.44 | 14.33 | 6.03 | 19.33 | 11.37 | 47.33 | 13.32 |
| 25 | 12.67 | 3.06 | 13.00 | 10.44 | 17.00 | 17.32 | 35.33 | 19.86 |
| 30 | 8.33 | 4.73 | 8.00 | 2.00 | 8.33 | 10.12 | 23.33 | 4.16 |
| 35 | 10.00 | 10.15 | 7.00 | 6.08 | 5.33 | 5.86 | 15.33 | 10.12 |
| 40 | 6.67 | 3.21 | 5.00 | 1.00 | 9.00 | 13.86 | 8.67 | 5.51 |
| 45 | 7.00 | 7.21 | 1.67 | 1.53 | — | — | 12.33 | 11.37 |
| 50 | — | — | — | — | — | — | 6.33 | 4.51 |

In conclusion the method of the invention enables rinse properties to be measured accurately for different compositions.

What is claimed is:
1. A method of measuring rinse properties of a composition from a surface, the method comprising:
applying a cosmetic treatment composition to a surface;
rinsing the surface with a first amount of water after applying the cosmetic treatment composition to the surface;
collecting a portion of the first amount of water after rinsing the surface with the first amount of water;
measuring a first turbidity of the portion of the first amount of water after collecting the portion of the first amount of water;
determining first rinse properties for the cosmetic treatment composition after measuring the first turbidity;
applying a second treatment composition to the surface after measuring the first turbidity;
rinsing the surface with a second amount of water after applying the second treatment composition to the surface;
collecting a portion of the second amount of water after rinsing the surface with the second amount of water;
measuring a second turbidity of the portion of the second amount of water after collecting the portion of the second amount of water;
determining second rinse properties for the second treatment composition after measuring the second turbidity; and comparing the first rinse properties and the second rinse properties to determine a relative rate of rinsing of the cosmetic treatment composition and the second treatment composition.

2. The method of claim 1, further comprising:
rinsing the surface with a second amount of water after measuring the first turbidity;
collecting a portion of the second amount of water after rinsing the surface with the second amount of water; and
measuring a second turbidity of the portion of the second amount of water after collecting the portion of the second amount of water.

3. The method of claim 2, further comprising waiting a time period after measuring the first turbidity and before rinsing the surface with the second amount of water, the time period being between 4 seconds and 120 seconds, inclusive.

4. The method of claim 1, wherein the first amount of water is from a flow of water.

5. The method of claim 1, further comprising correlating the portion of the first amount of water to the first amount of water.

6. The method of claim 1, wherein the surface is a portion of hair or a portion of skin.

7. The method of claim 1, wherein the cosmetic treatment composition is a structured composition that comprises a molecular orientation that forms a gel phase or a lamellar phase.

8. The method of claim 1, further comprising comparing the first turbidity and the second turbidity to determine a first change in turbidity.

9. The method of claim 8, further comprising:
comparing the first change in turbidity with the turbidity of pure water;
rinsing the surface with a third amount of water after determining that the first change in turbidity is greater than the turbidity of pure water;
collecting a portion of the third amount of water after rinsing the surface with the third amount of water; and
measuring a third turbidity of the portion of the third amount of water after collecting the portion of the third amount of water.

10. The method of claim 9, further comprising:
comparing the second turbidity and the third turbidity to determine a second change in turbidity; and
comparing the second change in turbidity to the turbidity of pure water.

11. A method of measuring rinse properties of a composition from a surface, the method comprising:
applying a first treatment composition to a surface;
rinsing the surface with a first amount of water after applying the first treatment composition to the surface;
collecting a portion of the first amount of water after rinsing the surface with the first amount of water;
measuring a first turbidity of the portion of the first amount of water after collecting the portion of the first amount of water;
rinsing the surface with a second amount of water after measuring the first turbidity;
collecting a portion of the second amount of water after rinsing the surface with the second amount of water;
measuring a second turbidity of the portion of the second amount of water after collecting the portion of the second amount of water;
comparing the first turbidity and the second turbidity to determine a first change in turbidity;
comparing the first change in turbidity with the turbidity of pure water;
rinsing the surface with a third amount of water after determining that the first change in turbidity is greater than the turbidity of pure water;
collecting a portion of the third amount of water after rinsing the surface with the third amount of water;
measuring a third turbidity of the portion of the third amount of water after collecting the portion of the third amount of water;
comparing the second turbidity and the third turbidity to determine a second change in turbidity;
comparing the second change in turbidity with the turbidity of pure water; and
determining a first rinse property of the first treatment composition after determining that the second change in turbidity is less than the turbidity of pure water.

12. The method of claim 11, further comprising:
applying a second treatment composition to the surface after determining the first rinse property;
rinsing the surface with a fourth amount of water after applying the second treatment composition to the surface;
collecting a portion of the fourth amount of water after rinsing the surface with the fourth amount of water; and
measuring a fourth turbidity of the portion of the fourth amount of water after collecting the portion of the fourth amount of water.

13. The method of claim 12, further comprising:
rinsing the surface with a fifth amount of water after measuring the fourth turbidity;
collecting a portion of the fifth amount of water after rinsing the surface with the fifth amount of water;
measuring a fifth turbidity of the portion of the fifth amount of water after collecting the portion of the fifth amount of water;
comparing the fourth turbidity and the fifth turbidity to determine a third change in turbidity;
comparing the third change in turbidity to the turbidity of pure water; and
rinsing the surface with a sixth amount of water after determining that the third change in turbidity is greater than the turbidity of pure water.

14. The method of claim 13, further comprising:
collecting a portion of the sixth amount of water after rinsing the surface with the sixth amount of water;
measuring a sixth turbidity of the portion of the sixth amount of water after collecting the portion of the sixth amount of water;
comparing the fifth turbidity and the sixth turbidity to determine a fourth change in turbidity;
comparing the fourth change in turbidity to the turbidity of pure water; and
determining a second rinse property of the second treatment composition after determining that the fourth change in turbidity is less than the turbidity of pure water.

15. The method of claim 14, further comprising determining a relative rate of rinsing between the first treatment composition and the second treatment composition.

16. The method of claim 14, further comprising performing a modification to the surface after determining the first rinse property and before applying the second treatment composition to the surface.

17. The method of claim 14, wherein:
the first treatment composition is a shampoo or a conditioner; and the second treatment composition is a shampoo or a conditioner.

18. The method of claim 14, further comprising applying a pre-wash solution to the surface before applying the first treatment composition to the surface, the pre-wash solution configured to remove contaminants from the surface.

19. The method of claim 14, further comprising:
waiting a first time period after measuring the first turbidity and before rinsing the surface with the second amount of water, the first time period being between 4 seconds and 120 seconds, inclusive; and
waiting a second time period after determining the first rinse property and before applying the second treatment composition, the second time period being between 4 seconds and 120 seconds, inclusive.

\* \* \* \* \*